United States Patent [19]

Dosch et al.

[11] 4,394,263
[45] Jul. 19, 1983

[54] CONNECTING DEVICE FOR PNEUMATIC AND/OR HYDRAULIC CIRCUITS IN COLUMN CHROMATOGRAPHY

[75] Inventors: Werner Dosch, Mainz; Heinz Wagner, Mainz-Marienbord, both of Fed. Rep. of Germany

[73] Assignee: Carlo Erba Strumentazione S.p.A., Rodano, Italy

[21] Appl. No.: 327,548

[22] Filed: Dec. 4, 1981

[30] Foreign Application Priority Data

Dec. 4, 1980 [DE] Fed. Rep. of Germany ....... 3045654

[51] Int. Cl.³ .............................................. B01D 15/08
[52] U.S. Cl. ................................... 210/198.2; 55/386
[58] Field of Search ....................... 210/198.2; 55/386

[56] References Cited

U.S. PATENT DOCUMENTS 3,119,251 1/1964 Bowers ................................ 55/386
3,150,517 9/1964 Kuffer et al. ........................ 55/386
3,922,223 11/1975 Burkhartsmeier ............... 210/198.2

FOREIGN PATENT DOCUMENTS 3617 of 0000 European Pat. Off. .
2520075 of 0000 Fed. Rep. of Germany .
2655387 of 0000 Fed. Rep. of Germany .
2806123 of 0000 Fed. Rep. of Germany .
2840612 of 0000 Fed. Rep. of Germany .
1346196 of 0000 France .
2407019 of 0000 France .
1771781 1/1970 United Kingdom .

OTHER PUBLICATIONS

J. Chromatography, 91 (1974) 603–612, RIJKS et al., "Characterization of Hydrocarbons in Complex Mixtures by Two-Dimensional Precision Gas Chrom."
Chromatographia, vol. 10, No. 8, Aug. 1977, 473–477, Muller et al., "Experience and Problems with Capillary Glass Columns etc."
Siemens MP 44, 1979, 7–8.

Primary Examiner—John Adee
Attorney, Agent, or Firm—Millen & White

[57] ABSTRACT

The invention relates to a connecting device for fluid circuits in column chromatography. To ensure an inert connection without dead volumes, the device comprises a glass or fused silica thick-wall body with an inner capillary channel connected to the outside through radial holes. In such holes, metal or fused silica capillaries are inserted and each fixed by means of a coupling carrying a capillary set screw and a coupling fixing screw, with said screws acting on opposite positions of said body wall.

15 Claims, 7 Drawing Figures

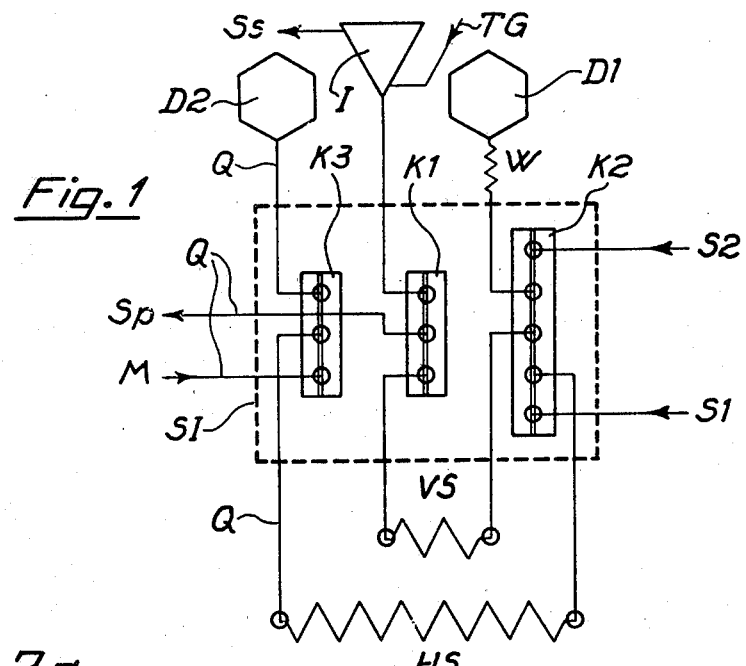
Fig. 1
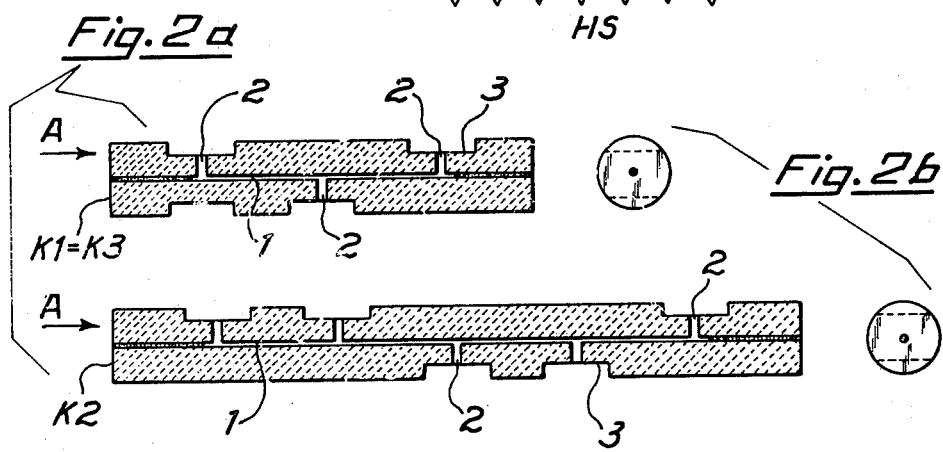
Fig. 2a
Fig. 2b
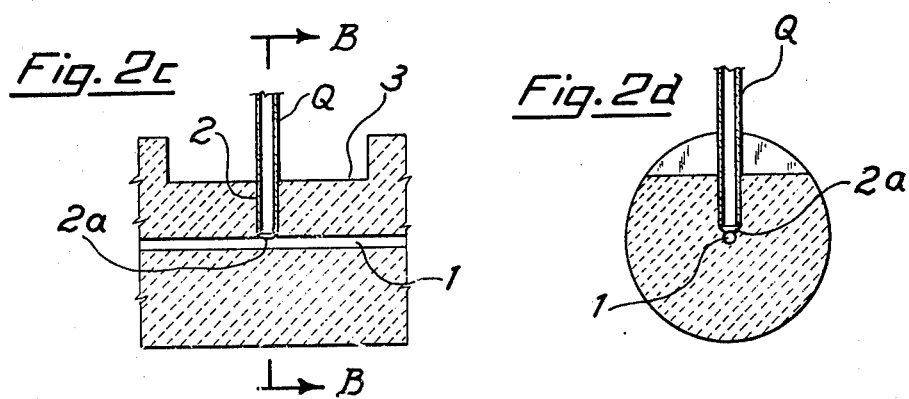
Fig. 2c
Fig. 2d

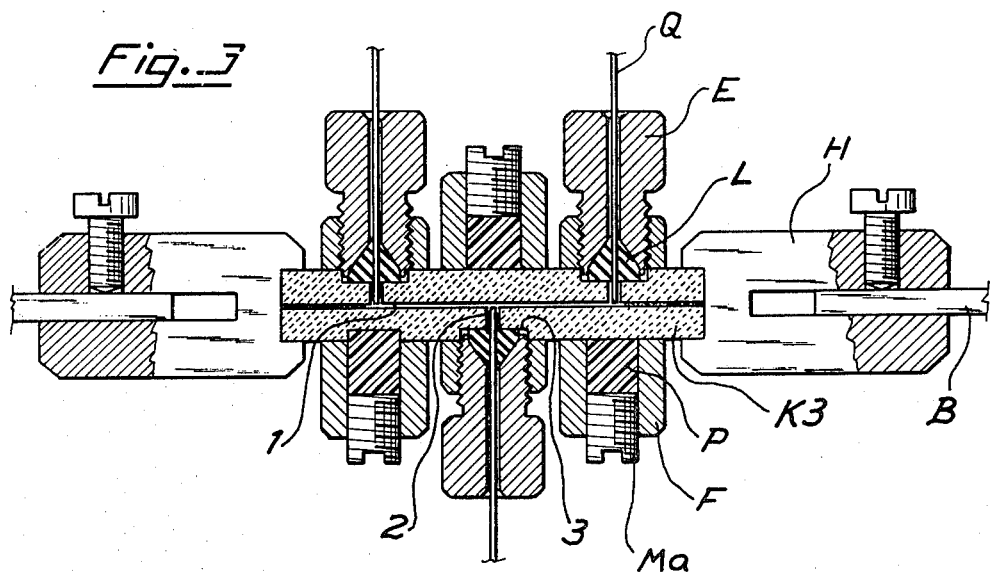
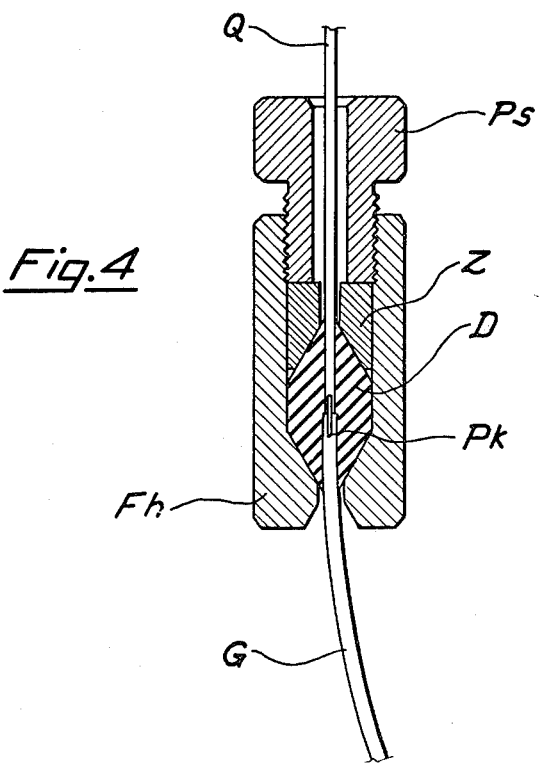

CONNECTING DEVICE FOR PNEUMATIC AND/OR HYDRAULIC CIRCUITS IN COLUMN CHROMATOGRAPHY

BACKGROUND OF THE INVENTION

1. Field of the Invention

This invention relates to a connecting device for pneumatic and/or hydraulic circuits to be used in the separation technique, especially in capillary column chromatography for systems of partition and commutation of the flow of fluid carrying the sample to be analyzed, wherein chemically inert gaskets and fittings are used.

In the case of gas chromatographic separations in a separation column or in several separation columns coupled in series or in parallel, said columns must be connected between each other and to one or more injectors and detectors, and even to supplementary gas pipings, i.e. pipings for make-up gas or pilot gas, to allow for a time regulated inversion of the gas flow under test from a separation column to another one, according to a known "Deans's commutation technique". In this case the relevant fittings must behave in a chemically inert way with respect to the fluid flows and must ensure a perfect seal without considerably departing from the internal diameter of the separation capillary column, so as to ensure an almost complete elimination of dead volumes. In this case, "dead volume" means the space not necessary for conveying fluid, in the parts of which said fluid flows in and out, and where the presence of the fluid or gas under test is prolonged (peak broadening), and wherein parts of the sample can be retained and fractions of already separated gas sample are mixed again. Dead volumes, for instance, appear in the points where the diameter of the gas piping increases, where bag extensions are formed in these pipings, where blind tubings are connected, and so on. In operation with one or more separation columns, the pneumatic circuits, which are differentiated from each other according to specific gas chromatographic functions, must be such as to be connected and optimized in a simple way, so that, in particular, also the insertion or substitution of separation glass capillary columns, which are delicate and expensive, can be performed in a way as to exclude damaging or complex operations.

It is known that in the most simple case of a gas chromatographic analysis, a sample vaporized in the injector or introduced therein already at the gaseous state, is conveyed by the carrier gas flow through a separation column, at the end of which a detector is provided. For this process, separation capillary columns are preferable to separation packed columns, due to their higher separation power.

Besides this simpler pneumatic circuit, i.e. injector→separation column→detector, several other pneumatic circuits are known, which can involve the use of one to two injectors, one to three separation columns, one to three detectors; in this case, for example, single separation columns can be washed in countercurrent while analysis is going on.

2. Description of the Prior Art

Pneumatic circuits of said type have been described for instance by D. R. Deans, Chromatographia 1 (1968), 18–22 (U.K. Pat. No. 1 236 937); W. Bertsch, HRC & CC 1 (1978), 85–91; 187–198; 289–300; G. Schomburg, "Gaschromatographie in Kapilläarsaulen", Max Planck Inst. für Kohlenforschung 40–42, 86 (1979); R. E. Kaiser, "Vorsäule in der Gaschromatographie", Selbstverlag Institut für Chromatographie; R. E. Kaiser "Trenncassetten zur Gas-Chromatographie", Chromatographia Vol. 7 (1974). A common peculiarity of this technique is the fact that several separation capillary columns are connected to injectors, detectors and to the necessary supplementary pipings. No inert fittings have been known up to now, by means of which said connections could be performed in such a way that diversified pneumatic circuits could be connected and disconnected according to analytical needs.

As a matter of fact, the presently known technique comprises welded fittings, and therefore, not detachable ones, or fittings having at least a metal section, and therefore, not inert with respect to all possible fluids. This known technique also includes a commutation system, especially for gas chromatographic columns, according to German patent application No. 2,655,387 to Siemens A. G. According to said system, the commutation of the gas flow from a pre-column to an auxiliary detector or to a main separation column, is carried-out by a pilot gas by means of a special fitting essentially consisting of a Pt/Ir capillary, which is positioned in another tube together with a coaxial gasket, said tube being provided, at its two ends which are insulated between each other by said gasket, with three fittings for the connection of separation capillary columns and other necessary tubings. By a suitable control of the pilot gas flow, dead volumes, which are unavoidable in such configurations, are made inefficient. Said system allows washing of the precolumn in countercurrent as well as connecting packed separation columns to the described double-tube central fitting, but it has limits due to its catalytic activity and to the specific pneumatic functions described in said patent.

SUMMARY OF THE INVENTION

The device of the present invention concerns a technical solution for directly connecting the ends of the capillary columns used for separation to the remaining gas chromatographic system. Said connections are necessary for using commutation systems of the columns, as for example, in the so-called "multi-dimentional gas chromatography". The basis of this technique is the principle of achieving optimal separation conditions, by means of series connected columns for the components of a mixture under analysis, in order to reduce the long time necessary for the optimal separation of all the components of samples having a complex composition. In this case, from a previously separated mixture in a first separation column (pre-column), fractions can be transferred at will to a second separation column (main column) and therein analyzed with high resolution power. Both separation columns can be provided with detectors. Commutations in columns of this type are performed by means of pilot gas, according to the method proposed by D. R. Deans and are carried out by means of electromagnetic valves and resistances to the gas flow, regulated by a time control placed out of the gas chromatographic oven. Considering the danger of disgregation reactions, of adsorption effects and so on, it is necessary to avoid the sample coming into contact with hot steel parts.

Furthemore, it is possible to eliminate undesired components before their entering into a main separation column, more sensitive to substances of this kind. The same device can be used to connect a column to more injectors or detectors.

The present invention has as an object providing a device by which pneumatic and/or hydraulic circuits, used in the separation technique and particularly in communication systems of the gas flow in capillary column chromatography, can be changed in a simple, quick and safe way, with a perfect chemical inertia, avoiding adsorption or thermal and catalytic transformation of the sample components.

According to the invention, this object is achieved by means of a connecting device for pneumatic and/or hydraulic circuits, to be used in the separation technique, in particular in capillary column chromatography, for systems of partition and commutation of the fluid flow carrying the sample to be analyzed, in which gaskets and fittings made of chemically inert material are used, wherein a pneumatic or hydraulic distribution panel is provided, comprising at least a mechanically stable glass or fused silica body, with thick wall, having a capillary channel, which presents a series of side fittings in the form of transversely extending holes, so as to form a multiple T-fitting, the holes of which, and possibly the front sections of the capillary channel, house the capillary tubes which convey gas or liquid, in such a way that their ends are easily removable, pneumatically closed and at least approximately free of dead volumes. The inlet of the holes in the thick-wall body are flattened to obtain a bearing surface for a gasket, while said thick-wall body carries holding couplings, each of which can be fixed in correspondence with a hole thereof and has a set screw adapted to secure in a sealing way the end of a tube inserted in a transversely extending hole, through a gasket pressing on said surface.

For gas tubings which come into contact with the gas flow under test, according to the invention, fused silica flexible capillaries are used; for other gas tubings, steel capillaries can serve as well. In gas chromagographs existing on the market, the distribution panel according to this invention is installed in the oven chamber. In a further embodiment, conventional ovens for gas chromatography can be dispensed with, if each of the separation columns, which is prolonged by means of fused silica flexible capillaries, is heated independently in a thermally insulated structure.

The advantages as obtained by this invention mainly consist of the fact that differentiated pneumatic circuits can be obtained in a way that gas chromatographic analyses are carried out in a system which is almost free from dead volumes, in a chemically insert material, so that for the substitution of separation capillary columns, preliminary preparations of the column ends are eliminated and it is possible to make insertion of substitution of one or more separation capillaries in a considerably easier way. Furthermore, the gas flow coming from the injector can be divided, in the pneumatic distribution panel, in a way necessary for gas chromatography measurements on capillary columns; all that results in the fact that the device can be used as parition system.

A particular advantage is obtained in non-vaporizing injection method of on-column type, by connecting the injector to the distribution panel by means of a fused silica capillary. In this type of injection, non volatile components or solid small portions of the same which can remain in the initial part of the separation capillary column, alter, by adsorption or chemical reaction, the subsequently analyzed samples.

In the known manner to actuate this method, the separation column is directly connected to the injector and can be damaged, for example by dirt particles coming from the solutions under test, and therefore it must be substituted or considerably cut down. This is not necessary if the injector is connected to a sufficiently long section of a fused silica flexible capillary for the drawing of the cold-injected solution under test. The capillary is connected to the separation column through one of the multiple T-fittings according to the invention. In case of pollution, the fused silica capillary can be easily substituted.

The distribution panel according to the invention, besides it being possible for use in any conventional gas chromatograph, provides for a new concept of the gas chromatographic equipment, on the basis of which it is possible to eliminate the oven, as currently used up to now, in case the four elements of the equipment i.e.: injector (—S), detector (—S), distribution panel, separation column (—S) are independently heated.

In this way it is also possible to obtain a spatial separation of said elements, which until now were integrated in the central oven of a gas chromatograph; this has the advantage of simplifying assembly in case pneumatic circuits have to be inserted, independently from space limitations of a given oven, in case of column substitution, of insertion of blocks for cooling and for connecting the gas chromatograph to other analytical instruments, for instance a mass spectrometer.

Further advantages are obtained by separating the glass capillary column or columns from the injector (s) and detector (s) by means of intermediate sections of fused silica capillaries and their connection to the distribution panel.

BRIEF DESCRIPTION OF THE DRAWINGS

FIG. 1 is a diagram showing a possible use of a device according to the invention.

FIGS. 2a, 2b, 2c, and 2d, are sections of an example of multiple fitting body element.

FIG. 3 is a section of a complete fitting.

FIG. 4 is a section of an axial fitting between columns.

DESCRIPTION OF THE PREFERRED EMBODIMENT

A general embodiment for the use of a system of column commutation is illustrated in FIG. 1. The distribution panel SI comprises three multiple T-fittings K1, K2 and K3, the side holes of which receive the gas tubes Q and the injector I, the detectors D1 and D2, the precolumn VS, the main column HS, the switch Sp, the make-up-gas line M and the two pilot gas tubes S1 and S2. W indicates a resistance for the gas flow before D1, $S_s$ the diaphragm washing, and TG the carrier gas inlet.

The gas under test, vaporized in I, is conveyed by the carrier gas towards direction K1 and, according to the position of the switch Sp, it is partly purged in the atmosphere and partly carried through the precolumn VS towards K2. From K2 the gas under test then reaches the detector D1, if pilot gas S1 pressure is kept higher than S2 pressure. Reversing this pressure ratio (Ss higher than S1), a portion of the gas flow under test outflowing from VS is conveyed through the main separation column HS to the detector D2, until the ratio of pilot gas pressure is reverted again (S1 higher than S2).

In the described operations, in which the gas under test can be analyzed in the detector D1 or in the detector D2, the pressure of the gas flow under test passing from the precolumn in K2 is higher than the pressure of each of the two operating pilot gases S1 and S2. Stopping the carrier gas flow, the precolumn can be rinsed in countercurrent thanks to overpressure existing in S1 and S2, through the diaphragm Ss and then be ready in a particularly quick way for a subsequent analysis, while still some portions of the already analysed gas flow through the main column towards the detector D2.

FIG. 1 only shows the essential characteristics of the distribution panel, for the chosen distribution example. The pressure regulators necessary for operation and the circuits of the different gas flows, as well as time electromagnetic valves, gas flow resistances and by-pass circuits are not shown in this figure, as their construction is generally known. The tubings, which convey gas to the distribution panel from the injector and from the two detectors, are constituted by fused silica flexible capillaries as well as the fittings between the distribution panel and the separation capillary columns. For the tubings indicated by S1 and S2, M and Ss, steel capillaries can be used.

FIGS. 2a and 2b illustrate embodiments of multiple T-fittings, objects of the invention, K1, K3 and K2 respectively, according to the circuit exemplified in FIG. 1. In the illustrated embodiment, there are three thick-wall bodies, having internal capillary passages 1 closed at their ends and provided with radial holes 2, which penetrate into the wall until reaching the capillary channel 1. The holes 2 correspond to the outer diameter of the capillaries to be inserted therein, which are fused silica or steel capillaries. The body is milled where the holes 2 are, to provide a smooth supporting surface 3. An advantageous fact is that, for the perforation of the fitting holes, for example by hard metal drills of 0.5 or 0.6 mm diameter, at the contact point with the capillary channel 1 which is approximately 0.3 mm diameter, a sort of neck 2a is obtained (see the enlargement in FIG. 2c or 2d). This neck prevents the fused silica or steel capillaries Q from being introduced too deeply into the holes 2 and from obstructing the capillary channel of the thick-wall body. Furthermore, it has been proved that, removing the hard metal drill, in correspondence to the surface 3 a slight bur occurs and the hole opening, then results larger; this makes easier the introduction of capilliary tubes Q.

For manufacturing multiple T-fittings, silicon-boron glass bodies are suitable, with a capillary channel of approx. 0.3 mm inner diameter and an external diameter of more than 4 mm. However, the bodies can also be made of other types of glass, silicate or fused silica glass.

FIG. 3 illustrates an embodiment, according to the invention, of pneumatic connections, substantially free of dead volumes, with a multiple T-fitting according to FIG. 2. The capillaries Q are kept in position by collar couplings F, each of which can be secured by a screw Ma to the multiple T-fitting with the insertion of a synthetic resin insert P. The insert P can rest on the cylindric surface or on a milled surface of the glass body. The fused silica or steel capillaries are introduced into the side holes 2 of the multiple T-fitting as far as they reach into the capillary channel 1 and are sealed by means of a conical gasket L and a pressure screw E, which pushes the gasket L on the milled surface 3 of the multiple T-fitting. Each of these multiple T-fittings is secured to a mounting plate B by means of blocking couplings H. To simplify assembling it is particularly advisable to make connections with the separation column or columns coming out from the bottom, while all the other gas tubings come out from the top of the multiple T-fitting.

For the gaskets L, graphite is preferably used. By means of the plastic coupling P and thanks to its specific position, it should be possible to avoid the danger of breakage in the multiple T-fitting. Besides being connected according to what illustrated in FIG. 3, some of the gas external tubings can also be connected to the ends of the multiple T-fitting, which in this case has the capillary end (s) open. The screw fittings, as illustrated in the shown example, can be modified in various ways, or in particular cases can be substituted at least partly by soldering (for example with silver chloride), by welding (for instance with intermediate sections of capillaries in Pt/Ir) or by adhesives, but in any case the advantage of the invention of variable assembling in blocks is reduced.

The branchings off of the circuits illustrated in FIG. 3, each consisting of a multiple T-fitting and tubings Q constituted by thin-wall capillaries, connected in a non-permanent way, can be used for conveying gases and liquids as well, with no leakage up to pressures of approximately 500 bar. The multiple T-fittings, therefore, can be used for hydraulic circuits as well, or as dividing heads for samples in high pressure liquid chromatography (HPLC) or for other separation techniques. Should glass not be advisable as inert material for these applications, the multiple T-fittings can also be made of metal.

FIG. 4 illustrates an example of a connection between a glass separation capillary column and a fused silica flexible capillary. The glass separation capillary column is connected at its top end G, without having its structure modified, to a fused silica capillary Q and surrounded by a gasket D with cone-shaped ends at both sides, which is is pressed in a container Fh by a pressure screw Ps, by means of an intermediate element Z. The introduction of a short capillary section of Pt/Ir (Pk) in the connection point of the capillaries G and Q has proved to be advantageous. The device also allows non-skilled operators to substitute glass separation capillary column, in a simple way and without any damage. The open end, according to FIG. 4, of the fused silica capillary Q is connected to the distribution panel according to FIGS. 1 and 3. The containers Fh are placed in a wired structure or in a sheets steel box, which at the same time strengthens and protects from mechanical actions the fragile glass separation capillary column; it can also allow its heating independently from the conventional gas chromatography oven.

Besides separation capillary columns, glass or metal packed columns can also be connected to the distribution panel object of the invention. For this aim, in any case, it is necessary to use capillary-reducing couplings of metal or fused silica, which are welded to the ends of the packed separation column, otherwise, the connection can be performed in a known way by means of gaskets as existing on the market.

The shown embodiments may undergo to various modifications and changes without departing from the spirit and scope of this invention.

We claim:

1. A connecting device for use in pneumatic and/or hydraulic circuits, to be used in separation techniques, as in capillary column chromatography, for systems of partition and commutation of a fluid flow carrying a sample to be analyzed, in which chemically inert gaskets and fittings are used, comprising: a pneumatic or hydraulic distribution panel (S1) which comprises at least a mechanically stable, thick wall glass or fused silica body (K1, K2, K3), having a capillary channel (1) therein, and further having a series of side fittings in the form of transverse holes (2), to define a multiple T-fitting, said transverse holes (2) housing capillary tubes (Q) adapted for conveying gas or liquid, and said capillary tubes (Q) being constructed such that their ends are easily removable, pneumatically sealed and substantially free from dead volumes; said holes (2) having an inlet in the thick-wall body (K1, K2, K3) which is flattened to provide a bearing surface (3) for a gasket, and said thick-wall body (K1, K2, K3) carrying holding couplings (F), each of which can be fixed in correspondence with a hole (2), and each coupling (F) having a set screw (E) adapted for sealingly securing the end of a tube (Q) inserted in a transverse hole (2) through a gasket (L) pressing on said bearing surface (3).

2. A device according to claim 1, wherein the internal diameter of said capillary channel (1) of said thick-wall body (K1, K2, K3), and of said connecting tubes (q), is equal to the diameter of the separation capillary columns with which said connecting device is to be used.

3. A device according to claim claim 1 or 2, wherein each of said transverse holes (2) in said thick-wall body (K1, K2, K3) have a neck (2a) at the connecting point with said capillary channel (1), on which neck each of said inserted tubes (Q) rests.

4. A device according to claims 1 or 2, wherein the inlet of said holes (2) in said thick-wall body (K1, K2, K3) is mill-flattened to provide a supporting surface (3) for a gasket.

5. A device according to claim 1, wherein said retaining couplings (F) are slidingly mounted on said thick-wall body, and are adapted for being directly or indirectly secured to said body by means of a screw (Ma) acting in a position diametrically opposed to said pressure set screw (E).

6. A device according to claim 5, wherein said screw (Ma) for securing each coupling (F), acts on the wall of said thick-wall body through a synthetic resin insert (P) interposed therebetween.

7. A device according to claim 1, 2, 5 or 6, wherein said tubes (Q), which come into contact with a carrier fluid flow, are fused silica flexible capillaries.

8. A device according to claim 1, 2, 5 or 6, wherein said distribution panel (S1) is adapted for being independently heated and further comprises heating means for independently heating said panel (S1).

9. A device according to claim 3, wherein the inlet of said holes (2) in said thick-wall body (K1, K2, K3) is mill-flattened to provide a supporting surface (3) for a gasket.

10. A device according to claim 3, wherein said tubes (Q), which come into contact with a carrier fluid flow, are fused silica flexible capillaries.

11. A device according to claim 4, wherein said tubes (Q), which come into contact with a carrier fluid flow, are fused silica flexible capillaries.

12. A device according to claim 3, wherein said distribution panel (S1) is adpated for being independently heated and further comprises heating means for independently heating such panel (S1).

13. A device according to claim 4, wherein said distribution panel (S1) is adapted for being independently heated and further comprises heating means for independently heating such panel (S1).

14. A device according to claim 7, wherein said distribution panel (S1) is adapted for being independently heated and further comprises heating means for independently heating such panel (S1).

15. A device according to claim 1, wherein said transverse holes (2) are located on the front part of the capillary channel.

* * * * *